US005559284A

United States Patent [19]

[11] Patent Number: 5,559,284

Matta et al.

[45] Date of Patent: Sep. 24, 1996

[54] METHOD FOR DETERMINING ELONGATIONAL VISCOSITY AND DYNAMIC SURFACE TENSION IN LIQUID SOLUTIONS

[75] Inventors: Joseph E. Matta, deceased, late of Bel Air, Md., by Karen A. Matta, administratrix; Raymond P. Tytus, Bel Air, Md.

[73] Assignee: The United States of America as represented by the Secretary of the Army, Washington, D.C.

[21] Appl. No.: 422,966

[22] Filed: Apr. 17, 1995

[51] Int. Cl.$^6$ .......................... G01N 15/02; G01N 15/14; G01N 13/02; G01N 11/00

[52] U.S. Cl. ....................... 73/64.52; 73/54.05; 73/865.5; 356/335

[58] Field of Search ............................... 73/61.43, 64.52, 73/54.02, 54.05, 54.06, 61.44, 61.45, 61.48, 64.55, 865.5, 865.8; 356/335, 336

[56] References Cited

U.S. PATENT DOCUMENTS

| | | | |
|---|---|---|---|
| 3,818,200 | 6/1974 | Pilhofer | 73/861.04 X |
| 3,869,208 | 3/1975 | Lorenz | 356/336 X |
| 4,110,043 | 8/1978 | Eisert | 377/11 |
| 4,300,044 | 11/1981 | Iribarne et al. | 250/282 |
| 4,343,551 | 10/1982 | Eisert | 377/10 |
| 4,670,137 | 6/1987 | Koseki et al. | 73/61.77 X |
| 4,761,074 | 8/1988 | Kohsaka et al. | 356/336 X |
| 4,774,037 | 9/1988 | Hendricks | 264/9 |
| 4,794,086 | 12/1988 | Kasper et al. | 73/61.71 X |
| 5,121,629 | 6/1992 | Alba | 73/61.41 X |
| 5,247,842 | 9/1993 | Kaufman et al. | 73/865.5 |

FOREIGN PATENT DOCUMENTS

| | | | |
|---|---|---|---|
| 154914 | 4/1982 | German Dem. Rep. | 73/64.52 |
| 24670 | 2/1980 | Japan | 73/64.52 |
| 205368 | 11/1967 | U.S.S.R. | 73/64.52 |
| 234711 | 1/1969 | U.S.S.R. | 73/64.52 |
| 568871 | 8/1977 | U.S.S.R. | 73/64.52 |
| 607132 | 5/1978 | U.S.S.R. | 73/64.52 |

OTHER PUBLICATIONS

*Patent Abstracts of Japan* Grp P678, vol. 12, No. 88 Abs pub. date Mar. 23, 1988 (62–222145) "Method and Apparatus for measuring Impurity in Liquid".
*Patent Abstracts of Japan* Grp. P. 777, vol. 12, No. 406 Abs pub. date Oct. 27, 1988 (63–144235) "Particle Counter".
*Patent Abstracts of Japan* Grp P. 830, vol. 13, No. 73 Abs pub. date Feb. 20, 1989 (63–259466) "Cell Analyzer".
*Patent Abstracts of Japan* Grp P1110, vol. 14, No. 445 Abs pub. date Sep. 25, 1990 (2–176562) "Analysis Apparatus".

*Primary Examiner*—Thomas P. Noland
*Attorney, Agent, or Firm*—Ulysses John Biffoni; Edward L. Stolarun

[57] ABSTRACT

Disclosed is a method for measuring intermolecular force related physical properties of an objective liquid such as elongational viscosity and dynamic surface tension, comprising the steps of atomizing neat liquids to a particle size in a gaseous fluid stream, measuring the particle size of the atomized neat liquid, determining an empirical expression based on known physical properties of the neat liquid and the atomization conditions, and using the empirical expression and identical atomization conditions to rapidly determine the unknown intermolecular force related physical properties of the objective liquid, the objective liquid being another neat liquid or a liquid in which a solute is dissolved.

18 Claims, 1 Drawing Sheet

METHOD FOR DETERMINING ELONGATIONAL VISCOSITY AND DYNAMIC SURFACE TENSION IN LIQUID SOLUTIONS

BACKGROUND OF THE INVENTION

1. Field of the Invention

The present invention relates to methods and apparatus for measuring and testing the physical properties of materials and more particularly for measuring the elongational viscosity and dynamic surface tension of liquid solutions.

2. Brief Description of the Prior Art

Although various methods exist to characterize the elongational viscosity and to measure the dynamic surface tension of a liquid, none of these methods are conducted within the time scale associated with liquid atomization. This disclosure describes a novel technique from which one can characterize the elongational behavior of a Newtonian fluid or dilute polymer solution, and also measure the dynamic surface tension of a fluid, both within the time scale associated with fluid atomization.

Although other methods of characterizing the extensional flow behavior of a solution exist, e.g. tubeless syphon, impinging jets, falling cylinder, and spin rheometer, only the impinging jet method is suitable for dilute solutions. This method, however, is often unsuitable for low viscosity liquids and polymer solutions due to inertials effects and flow instabilities that occur at higher rates of deformation. Dynamic surface tension measurements are possible using a bubble growth technique, but is also limited to a time scale much larger than that associated with liquid atomization. Thus, in order to investigate the elongational viscosity and dynamic surface tension at high rates of deformation, a novel spray/particle sizing method was developed.

Previous studies of liquid jet breakup in air have established relationships for the resultant particle size, usually, in terms of the Mass Median Diameter (MMD) and as a function of the physical properties of the liquid and air over a range of liquid and air flow rates. In most cases only neat, i.e. fluids without polymer or surfactant additives liquids, have been investigated. When, however, liquid/surfactant blends and dilute polymer solutions are used in jet breakup studies the dynamic surface tension and the elongational viscosity of the polymer solution would affect the resultant MMD.

SUMMARY OF THE INVENTION

It is the object of the present invention to provide a means to measure the dynamic surface tension of a liquid containing surfactant in a time scale shorter than any other known technique.

It is a further object of the present invention is to provide a means to measure the static surface tension of neat liquids without regard to the wettability of the liquid as required by most conventional techniques.

It is a further object of the present invention to measure the effective elongational viscosity of a dilute polymer solution at high rates of deformation.

It is a further object of the present invention to vary the dynamic rate by adjusting the wind speed.

It is a further object of the present invention that can be used with much lower viscosity solutions than possible available with commercially available instrumentation.

In the present invention an empirical expression, derived from neat fluids atomized in an air stream, relates the resultant drop size, physical properties of the fluid, and atomization conditions to determine either surface tension or elogational viscosity.

$$MMD = 15285.4 \, ST^{0.725} \, ET^{0.095} \, AV^{-1.75} \quad \text{eq(1)}$$

wherein MMD is expressed in microns, ST is liquid surface tension in dynes/cm, ET is effective Trouton elongational viscosity in units of poise and AV is air velocity in m/sec.

$$ST = 3.46 \times 10^{-6} \, MMD^{1.32} \, ET^{-0.13} \, AV^{2.32} \quad \text{eq(2)}$$

wherein MMD is expressed in microns, ST is liquid surface tension in dynes/cm, ET is effective Trouton elongational viscosity in units of poise and AV is air velocity in m/sec.

$$ET = 6.74 \times 10^{-41} \, MMD^{9.67} \, ST^{-7.24} \, AV^{16.97} \quad \text{eq(3)}$$

wherein MMD is expressed in microns, ST is liquid surface tension in dynes/cm, ET is effective Trouton elongational viscosity in units of poise and AV is air velocity in m/sec.

For the purposes of this disclosure, "elongational viscosity" is a measurement of that property of a liquid which enables it to resist shear stress in a longitudinal direction. Dynamic surface tension is a measurement of the tendency of a liquid to bring its volume into a form having the least possible surface area. Both of these above defined characteristics result from intermolecular forces and the method of this invention is also applicable to other similar liquid characteristics resulting from such intermolecular forces.

BRIEF DESCRIPTION OF THE DRAWING

The invention is further described with reference to the accompanying drawings in which.

DETAILED DESCRIPTION

Figure 1:
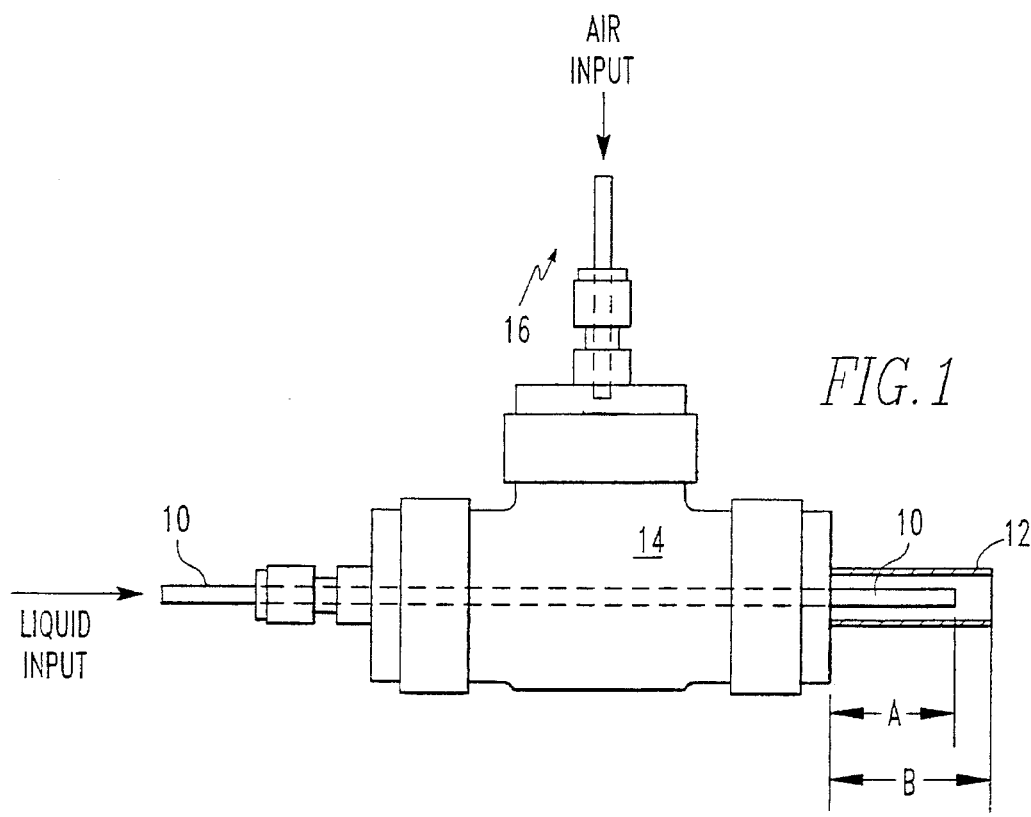
FIG. 1 is a plan view of an apparatus used to carry out the method of the present invention.

Referring to FIG. 1, there is shown a small scale coaxial liquid jet/air stream system using a Swagelok union tee for 1 inch diameter tubes. The capillary tube 10 inside diameter is 0.094 inches and is 6 inches long. The tube is centered in a 0.5 inch diameter TEFLON tube 12. Distance "A" is preferably about 1.9 cm and distance "B" is preferably 2.5 cm. Air input through another capillary tube 16 to the system fills volume 14 with pressurized air and can be regulated to produce air velocities up to 50 m/sec on exiting between TEFLON tube 12 and liquid capillary tube 10 as measured using a pitot tube. Liquid input through capillary tube 10 is supplied by a constant volume infusion pump with two 50 cc syringes at the downstream side. Volumetric flow rates as high as 83 cc/min can be obtained. The liquid jet stream and the gaseous fluid stream flow coaxially in the upstream section of the capillary tube 10 producing breakup of the liquid jet.

Liquid jet breakup MMD's were determined using a Malvern Particle Sizer which measured the resultant particle size distribution in real time. A laser beam from the Sizer transmitter was directed toward the particle spray which diffracted the incident beam. A receiving lens focuses the diffracted light onto a photodetector array. A computer software package than calculates and displays the resultant MMD. The liquid jet/air stream was positioned such that the center of the teflon tube was 9 cm from the front of the Malvern receiving lens and 2 cm normal to the laser beam. This 2 cm displacement was sufficient to insure complete atomization as evident from high speed flash photographs of the liquid spray.

Figure 2:
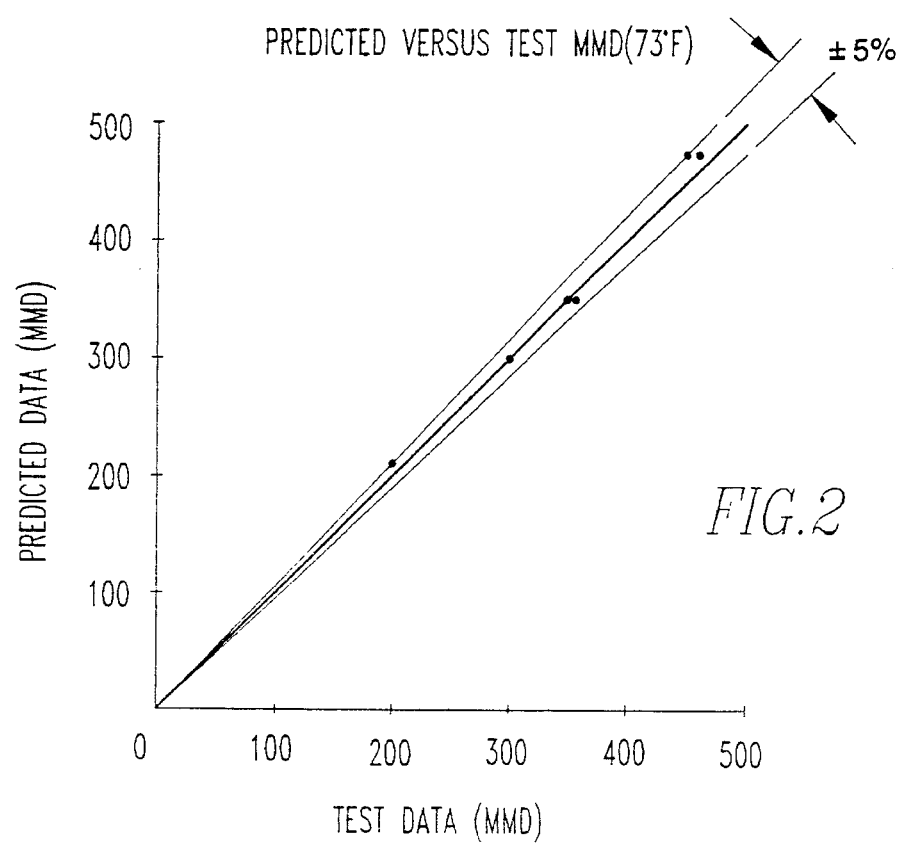
FIG. 2 is a graph showing predicted MMD data from an equation disclosed herein vs. actual MMD data.

Three neat liquids were used to establish an empirical relationship for MMD as a function of liquid physical properties. Table 1 lists the liquids and the associated physical properties that were varied. A total of 30 tests were performed in order to obtain a sufficient data base. Test results were then correlated using a multiple linear regression technique. The resultant equation is $$MMD = 15285.4 \, ST^{0.725} \, ET^{0.095} \, AV^{-1.75} \qquad \text{eq(1)}$$

Wherein MMD is expressed in microns, ST is the liquid surface tension (dynes/cm), ET is the effective Trouton elongational viscosity i.e. for a Newtonian fluid 3 times the shear viscosity in units of poise, and AV is the air velocity (m/sec). FIG. 2 shows the test MMD data plotted against the predicted MMD using equation (1). A good correlation is indicated. It was also possible to correlate the data by treating either the surface tension or the effective Trouton viscosity as the dependent variable, and resulted in the following two expressions, i.e.

$$ST = 3.46 \times 10^{-6} \, MMD^{1.32} \, ET^{-0.13} \, AV^{2.32} \qquad \text{eq(2)}$$

and $$ET = 6.74 \times 10^{-41} \, MMD^{9.67} \, ST^{-7.24} \, AV^{16.97} \qquad \text{eq(3)}$$

wherein the units are the same as described for eq(1). The time scale of the process can easily be determined from photographs of the liquid jet. The measured length of the jet and average wind speed can be used to estimate the breakup time of the process.

With Equations 2 and 3 and MMD measurements obtained with the spray/particle sizing system, it is now possible to deduce a dynamic surface tension or an effective elongational viscosity. Equation 2 is used to deduce the dynamic surface tension of a Newtonian liquid once the shear viscosity is obtained using standard viscometric techniques. Equation 3 is used to deduce an effective elongational viscosity of a dilute polymer solution once the steady state surface tension is measured using any standard technique.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

TABLE 1

| Liquid | Surface Tension (dynes/cm) | Trouton Viscosity (poise) |
| --- | --- | --- |
| Distilled Water | 69 | .027 |
| Peg-200 | 40.2 | 1.56 |
| 34% (ETOH)/Water | 36.3 | .03 |

What is claimed is:

1. A method for determining intermolecular force related physical properties of an objective liquid, comprising the steps of:
   (a) atomizing a neat liquid to a particle size in a gaseous fluid stream, said neat liquid having known intermolecular force related physical properties;
   (b) measuring the particle size of said atomized neat liquid;
   (c) determining an empirical expression based on the known physical properties of said neat liquid and the atomization conditions; and
   (d) using said empirical expression and identical atomization conditions to determine said intermolecular force related physical properties of said objective liquid.

2. The method of claim 1, wherein the intermolecular force related physical property determined is elongational viscosity.

3. The method of claim 2 wherein the objective liquid is a Newtonian fluid.

4. The method of claim 2 wherein the objective liquid is a polymer solution.

5. The method of claim 2, wherein said objective liquid contains surfactant.

6. The method of claim 1, wherein the intermolecular force related physical property determined is dynamic surface tension.

7. The method of claim 6 wherein the objective liquid is a Newtonian fluid.

8. The method of claim 6 wherein the objective liquid is a polymer solution.

9. The method of claim 6, wherein said objective liquid contains no surfactant.

10. The method claim 1 wherein the gaseous fluid stream is an air stream.

11. The method of claim 10 wherein the liquid particle size is defined in terms of mass median diameter (MMD) and the following relationship exists:

$$MMD = 15285.4 \, ST^{0.725} \, ET^{0.095} \, AV^{-1.75} \qquad \text{eq(1)}$$

wherein MMD is expressed in microns, ST is liquid surface tension in dynes/cm, ET is effective Trouton elongational viscosity in units of poise and AV is air velocity in m/sec.

12. The method of claim 10 wherein the liquid particle size is defined in terms of mass median diameter (MMD) and the following relationship exists:

$$ST = 3.46 \times 10^{-6} \, MMD^{1.32} \, ET^{-0.13} \, AV^{2.32} \qquad \text{eq(2)}$$

wherein MMD is expressed in microns, ST is liquid surface tension in dynes/cm, ET is effective Trouton elongational viscosity in units of poise and AV is air velocity in m/sec.

13. The method of claim 10 wherein the liquid particle size is defined in terms of mass median diameter (MMD) and the following relationship exists:

$$ET = 6.74 \times 10^{-41} \, MMD^{9.67} \, ST^{-7.24} \, AV^{16.97} \qquad \text{eq(3)}$$

wherein MMD is expressed in microns, ST is liquid surface tension in dynes/cm, ET is effective Trouton elongational viscosity in units of poise and AV is air velocity in m/sec.

14. The method of claim 1 wherein the liquid is atomized by causing said liquid to flow in a jet stream generally coaxially with the gaseous fluid stream.

15. The method of claim 14, wherein the gaseous fluid flows from a first capillary tube into a contained volume and then into a tube, said tube coaxially surrounding a second capillary tube, said second capillary tube containing said liquid jet stream.

16. The method of claim 15, wherein an atomized liquid particle stream is produced by the intersection of the liquid jet stream and the gaseous fluid stream and particle size is measured by directing a laser beam at the particle stream after which light from said laser beam is focussed on a photodetector display.

17. The method of claim 1, wherein the objective liquid is a neat liquid.

18. The method of claim 1, wherein the objective liquid is a liquid in which a solute is dissolved.

* * * * *